(12) United States Patent
Tsukagoshi et al.

(10) Patent No.: US 8,798,227 B2
(45) Date of Patent: Aug. 5, 2014

(54) MEDICAL IMAGE PROCESSING APPARATUS AND X-RAY COMPUTED TOMOGRAPHY APPARATUS

(75) Inventors: Shinsuke Tsukagoshi, Nasushiobara (JP); Kazumasa Arakita, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/323,866

(22) Filed: Dec. 13, 2011

(65) Prior Publication Data

US 2012/0093278 A1    Apr. 19, 2012

Related U.S. Application Data

(63) Continuation of application No. PCT/JP2011/073556, filed on Oct. 13, 2011.

(30) Foreign Application Priority Data

Oct. 15, 2010    (JP) ................................ 2010-232826

(51) Int. Cl.
    *A61B 6/00*    (2006.01)
(52) U.S. Cl.
    USPC ............................................. 378/4; 382/131
(58) Field of Classification Search
    USPC .......................................................... 378/4
    See application file for complete search history.

(56) References Cited

U.S. PATENT DOCUMENTS

| | | | | | |
|---|---|---|---|---|---|
| 4,920,573 | A | * | 4/1990 | Rhodes et al. | 382/131 |
| 5,253,171 | A | * | 10/1993 | Hsiao et al. | 378/4 |
| 5,371,778 | A | * | 12/1994 | Yanof et al. | 378/4 |
| 5,531,520 | A | * | 7/1996 | Grimson et al. | 382/131 |
| 5,699,799 | A | * | 12/1997 | Xu et al. | 600/407 |
| 5,734,384 | A | * | 3/1998 | Yanof et al. | 345/424 |
| 5,825,908 | A | * | 10/1998 | Pieper et al. | 382/131 |
| 5,883,933 | A | * | 3/1999 | Goto et al. | 378/62 |
| 5,970,504 | A | | 10/1999 | Abe et al. | |
| 6,144,972 | A | | 11/2000 | Abe et al. | |

(Continued)

FOREIGN PATENT DOCUMENTS

| | | |
|---|---|---|
| JP | 11-328433 | 11/1999 |
| JP | 2000-201921 | 7/2000 |

(Continued)

OTHER PUBLICATIONS

Internationa Search Report mailed on Jan. 17, 2012, in PCT/JP2011/073556, filed Oct. 13, 2011.

(Continued)

*Primary Examiner* — Courtney Thomas
(74) *Attorney, Agent, or Firm* — Oblon, Spivak, McClelland, Maier & Neustadt, L.L.P.

(57) ABSTRACT

According to one embodiment, it is an subject to reduce the occasion that a region of interest falls outside an image due to the influence of respiratory motion or pulsation. A medical image processing apparatus causes an slice image generation unit to generate a series of slice images from a series of volume data files associated with a three-dimensional region of an subject, and causes a slice position determination unit to determine each of a plurality of slices respectively corresponding to the slice images based on the position of a specific region included in the plurality of volume data files.

10 Claims, 12 Drawing Sheets

(56) References Cited

U.S. PATENT DOCUMENTS

| | | | |
|---|---|---|---|
| 6,154,518 A * | 11/2000 | Gupta | 378/62 |
| 6,363,134 B1 | 3/2002 | Suzuki | |
| 6,421,413 B1 * | 7/2002 | Knoplioch et al. | 378/19 |
| 6,496,560 B1 * | 12/2002 | Lin et al. | 378/62 |
| 6,643,533 B2 * | 11/2003 | Knoplioch et al. | 600/407 |
| 6,757,417 B2 * | 6/2004 | Licato et al. | 382/131 |
| 6,842,638 B1 * | 1/2005 | Suri et al. | 600/425 |
| 7,496,222 B2 * | 2/2009 | Mussack et al. | 382/131 |
| 7,515,675 B2 * | 4/2009 | Garms et al. | 378/4 |
| 2002/0118869 A1 * | 8/2002 | Knoplioch et al. | 382/131 |
| 2004/0249270 A1 * | 12/2004 | Kondo et al. | 600/425 |
| 2005/0180540 A1 * | 8/2005 | Mukumoto | 378/4 |
| 2005/0203372 A1 * | 9/2005 | Janssen et al. | 600/407 |
| 2007/0248319 A1 | 10/2007 | Sakaguchi | |
| 2009/0003676 A1 | 1/2009 | Li | |
| 2009/0028409 A1 * | 1/2009 | Tsukagoshi et al. | 382/131 |

FOREIGN PATENT DOCUMENTS

| | | |
|---|---|---|
| JP | 2005-204959 | 8/2005 |
| JP | 2006-68350 | 3/2006 |
| JP | 2007-260391 | 10/2007 |
| JP | 2007-282945 | 11/2007 |
| JP | 2009-00153 | 1/2009 |
| JP | 2009-207541 | 9/2009 |
| JP | 2011-120825 | 6/2011 |
| WO | WO 2009/096290 | 8/2009 |

OTHER PUBLICATIONS

Chinese Office Action issued Dec. 10, 2013 in corresponding Chinese Application No. 201180002863.7 (with English Translation), (37 pages).

* cited by examiner

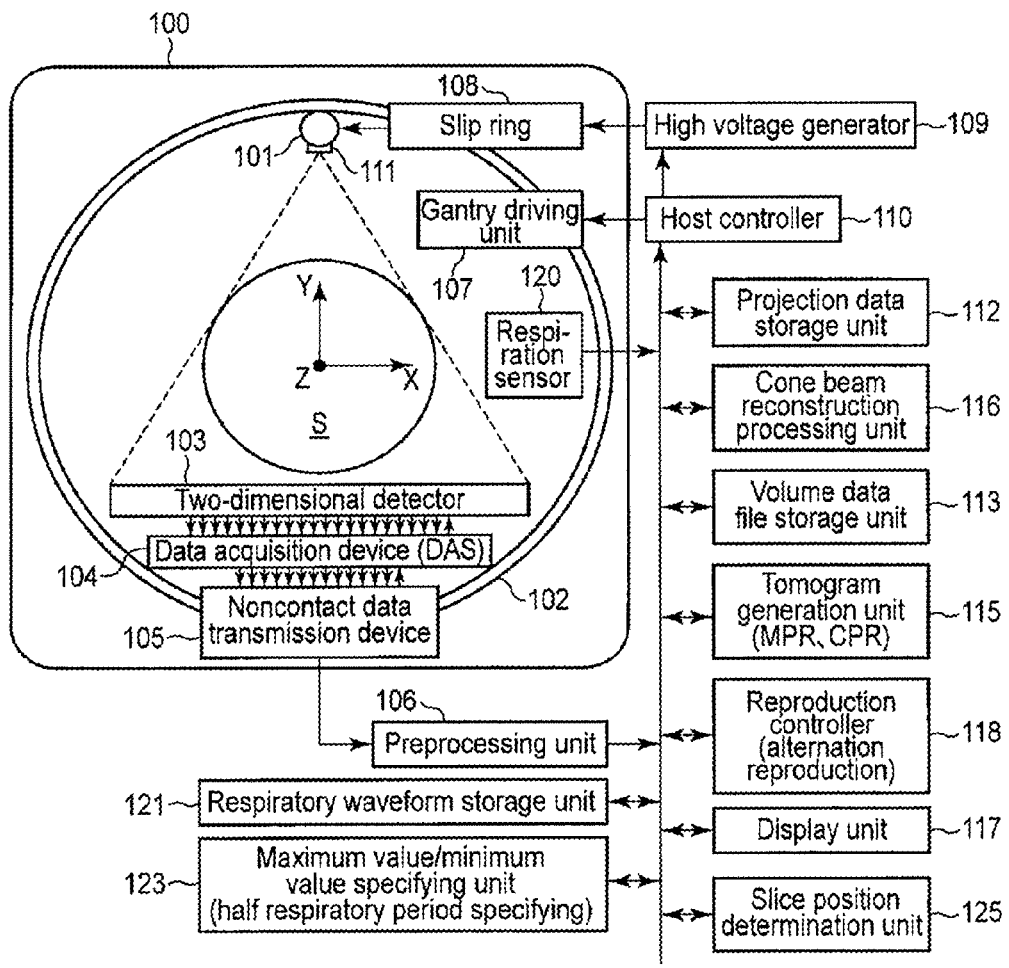
F I G. 1

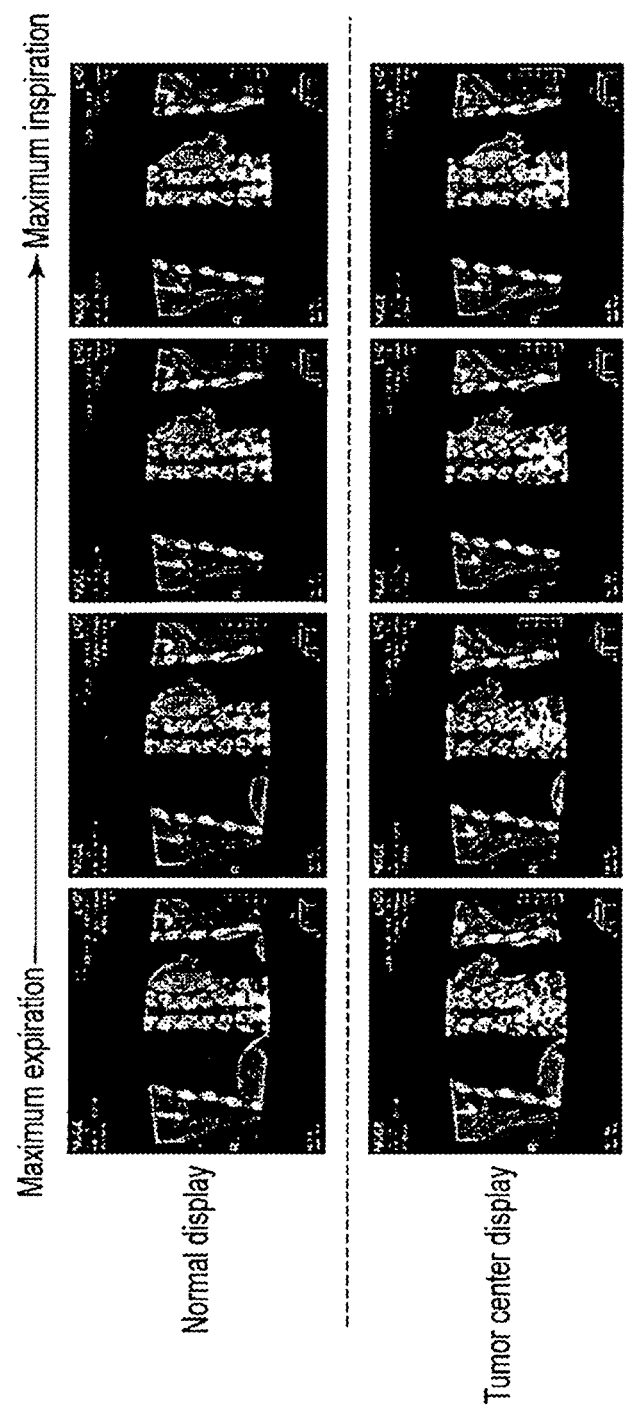
F I G. 15

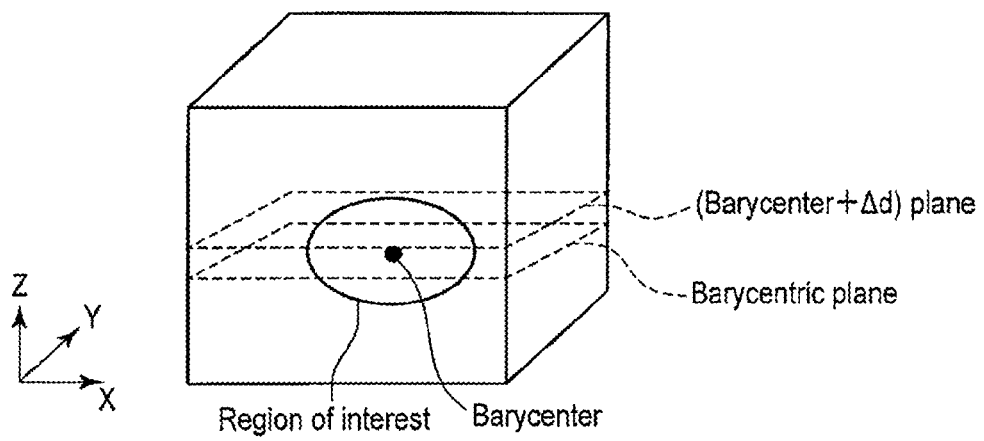
F I G. 16
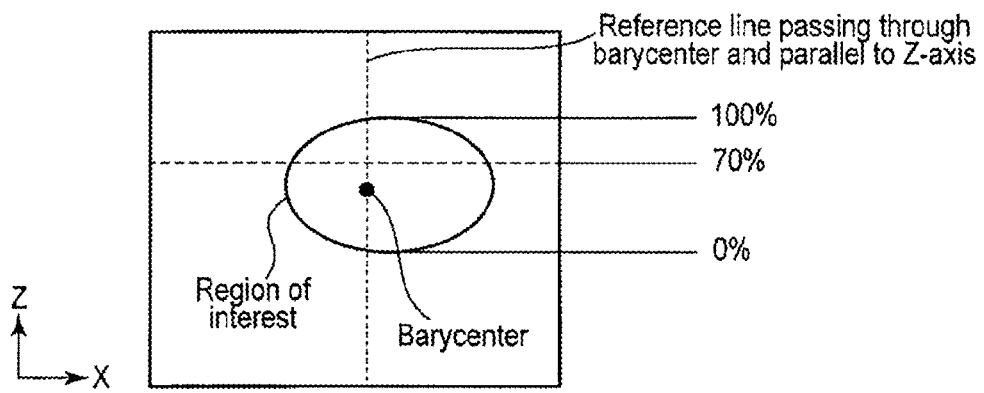
F I G. 17

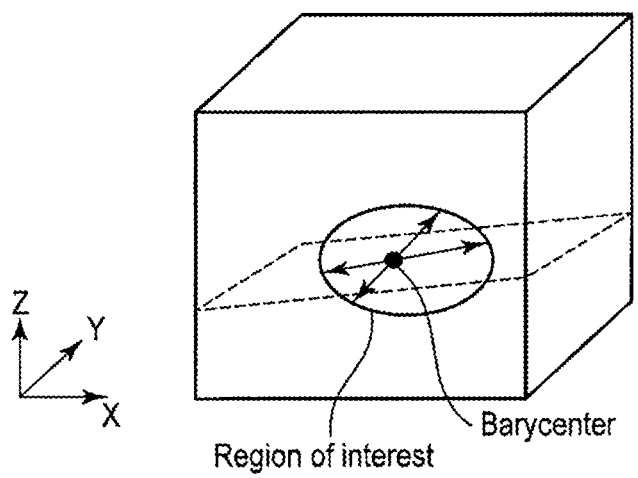
F I G. 20
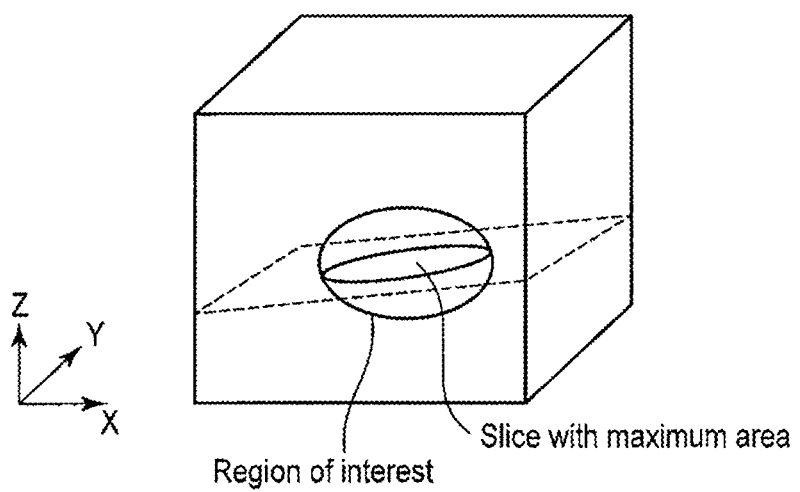
F I G. 21

MEDICAL IMAGE PROCESSING APPARATUS AND X-RAY COMPUTED TOMOGRAPHY APPARATUS

CROSS REFERENCE TO RELATED APPLICATIONS

This application is a Continuation Application of PCT Application No. PCT/JP2011/073556, filed Oct. 13, 2011 and based upon and claiming the benefit of priority from prior Japanese Patent Application No. 2010-232826, filed Oct. 15, 2010, the entire contents of all of which are incorporated herein by reference.

FIELD

Embodiments described herein relate generally to a medical image processing apparatus and an X-ray computed tomography apparatus.

BACKGROUND

Recently, ultrasonic diagnostic apparatuses, X-ray computed tomography apparatuses (CT), and magnetic resonance imaging apparatuses (MRI) have been able to repeatedly acquire data, with high time resolution, on which three-dimensional images are based. Such an apparatus will be described as an X-ray computed tomography apparatus here. This apparatus reconstructs a temporal series of volume data files based on repeatedly acquired projection data by a cone beam reconstruction method or the like. The apparatus generates a series of slice images based on a series of volume data files by MPR (Multi Planar Reconstruction) processing or the like. The series of slice images are reproduced as a moving image.

A region of interest (ROI) may fall outside a slice image due to respiratory motion, pulsation, or the like. During moving image reproduction, the adhesion region between the aorta and a tumor is not depicted in a slice image in some period due to, for example, three-dimensional movement of the tumor and aorta caused by respiratory motion.

CITATION LIST

Patent Literature

Patent Literature 1: Jpn. Pat. Appln. KOKAI Publication No. 2007-282945

BRIEF DESCRIPTION OF THE DRAWINGS

FIG. 1 is a view showing the arrangement of an X-ray computed tomography apparatus including a medical image processing apparatus according to an embodiment.

FIG. 15 is a view showing the effects obtained by this embodiment in comparison with the prior art.

FIG. 16 is a view showing a slice example set by the first automatic slice setting mode in FIG. 7.

FIG. 17 is a view showing a slice example set by the first automatic slice setting mode in FIG. 7.

FIG. 20 is a view showing a slice example set by the second automatic slice setting mode in FIG. 8.

FIG. 21 is a view showing a slice example set by the second automatic slice setting mode in FIG. 8.

DETAILED DESCRIPTION

Figure 2:
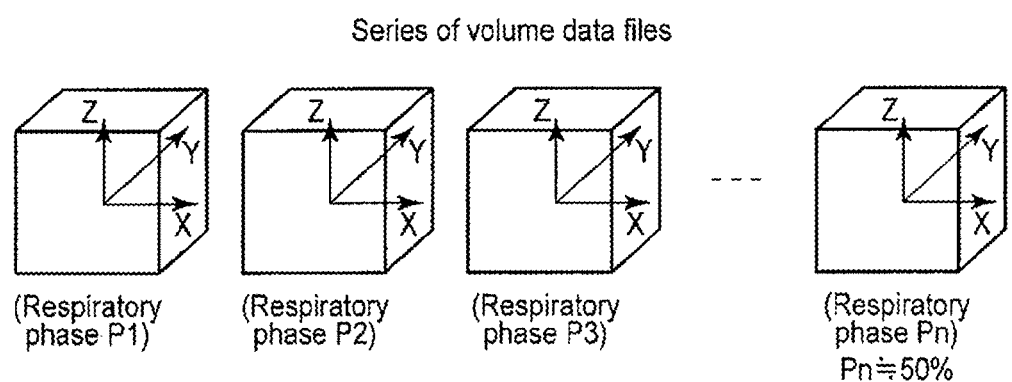
FIG. 2 is a view showing a series of volume data files generated by a cone beam reconstruction processing unit in FIG. 1.

In general, a medical image processing apparatus according to this embodiment will be described below with reference to the accompanying drawings. The medical image processing apparatus causes an image generation unit to generate a series of slice images from a series of volume data files associated with a three-dimensional region of a subject, and causes a slice determination unit to determine each of a plurality of slices respectively corresponding to the slice images based on the position of the specific region included in the plurality of volume data files.

Note that the medical image processing apparatus according to this embodiment is designed to process a series of volume data files associated with a three-dimensional region of an subject, which are repeatedly generated by a medical image generator such as an X-ray computed tomography apparatus, magnetic resonance imaging apparatus (MRI), ultrasonic diagnostic apparatus, or X-ray diagnostic apparatus. The medical image processing apparatus according to this embodiment is incorporated in such a medical image generator or provided independently. When provided independently, the medical image processing apparatus according to this embodiment is connected to an electrical communication line such as a LAN and receives a series of volume data files from an in-hospital or out-of-hospital picture archiving and communication system (PACS) via the electrical communication line. Assume that in the following description, the medical image processing apparatus is incorporated in an X-ray computed tomography apparatus.

FIG. 1 is a block diagram showing the arrangement of the X-ray computed tomography apparatus including the medical image processing apparatus according to this embodiment. A gantry unit 100 includes a rotating frame 102 which is rotatably supported. The rotation center axis of the rotating frame 102 is defined as the Z-axis. The Y-axis is defined to be perpendicular to the Z-axis passing through an X-ray focus and the center of a detector 103 (to be described later). The X-axis is defined so as to be perpendicular to the Y- and Z-axes.

A gantry driving unit 107 generates a driving signal for rotating/driving the rotating frame 102 under the control of a host controller 110. A cone beam X-ray tube 101 and a two-dimensional detector (also called an area detector) 103 are amounted on the rotating frame 102 so as to face each other through a columnar imaging area S centered on the Z-axis. The subject placed on the top of a bed (not shown) is placed in the imaging area S. The subject is placed such that its body axis almost coincides with the Z-axis. A high voltage generator 109 supplies a tube current to the X-ray tube 101 and also applies a high voltage to it under the control of the host controller 110. With this operation, the X-ray tube 101 generates X-rays from a focus F. An X-ray stop 111 shapes the X-rays generated by the cone beam X-ray tube 101 into a quadrangular pyramidal shape. The subject is irradiated with the X-rays shaped into the quadrangular pyramidal shape. The two-dimensional detector 103 includes a plurality of X-ray detection element arrays. The plurality of X-ray detection element arrays are juxtaposed in the Z-axis direction. Each X-ray detection element array is arranged in an arc centered on the X-ray focus F. A data acquisition device 104 generally called a DAS (data acquisition system) is connected to the two-dimensional detector 103.

The data acquisition device 104 is provided with, for each channel, an I-V converter for converting a current signal from each channel of the two-dimensional detector 103 into a voltage, an integrator which periodically integrates the voltage signal in synchronism with the irradiation period of X-rays, an amplifier which amplifies an output signal from the integrator, and an analog/digital converter which converts an output signal from the preamplifier into a digital signal.

A preprocessing unit 106 is connected to the output of the data acquisition device 104 via a noncontact data transmission device 105 which mediates an optical or magnetic element. The preprocessing unit 106 executes preprocessing, e.g., correcting sensitivity nonuniformity between channels and correcting an extreme decrease in signal intensity or signal omission due to an X-ray absorber, mainly a metal portion, with respect to the data detected by the data acquisition device 104. The data (projection data) output from the preprocessor 106 which has undergone the preprocessing is stored in a projection data storage unit 112.

In this embodiment, a so-called 4D dynamic scan is executed under the control of host controller 110. In a 4D dynamic scan, the rotating frame 102 is continuously rotated around an subject, together with the X-ray tube 101 and the two-dimensional detector 103, during an imaging period designated in advance. During the imaging period, the X-ray tube 101 generates X-rays continuously or in the form of pulses, and the two-dimensional detector 103 repeatedly detects X-rays. Note that a period during which the X-ray tube 101 rotates about 360° or (180°+fan angle) will be referred to as a scan period (first period). A single volume data file is reconstructed from projection data in the angle range of 360° or (180°+fan angle). A fan angle is an X-ray spread angle in an X-Y plane centered on an X-ray focus.

A cone beam reconstruction processing unit 116 reconstructs a plurality of volume data files obtained by expressing CT value distributions in a three-dimensional coordinate system by, for example, a cone beam reconstruction method based on the projection data stored in the projection data storage unit 112 under the control of the host controller 110. As described above, each volume data file is reconstructed from projection data in the angle range of 360° or (180°+fan angle). The angle ranges of projection data used to reconstruct a plurality of volume data files are shifted from each other by 30°. Accordingly, the imaging times of the plurality of volume data files are shifted from each other by the time required for rotation of 30°. Typically, the imaging time is defined as the time when projection data corresponding to almost the central angle of the angle range of projection data used for reconstruction is acquired. If a scan period is a time width (first period) required for the rotation of the angle range of projection data used for reconstruction, a volume data file is generated in the second period shorter than the first period. A series of volume data files are stored in a volume data file storage unit 113.

Figure 3:
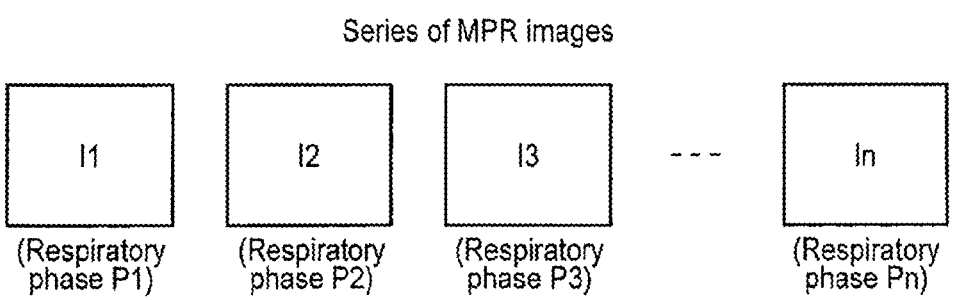
FIG. 3 is a view showing a series of MPR images generated by a slice image generation unit in FIG. 1.

As shown in FIG. 3, a slice image generation unit 115 generates a series of a plurality of slice images respectively corresponding to a series of a plurality of volume data files by so-called MPR processing (Multi Planar Reconstruction Processing) or CPR processing (Curved Planar Reconstruction Processing) matching display on a display unit (display) 117. The imaging time of a slice image coincides with the imaging time of a volume data file on which the slice image is based. The data of a plurality of generated slice images are stored in the volume data file storage unit 113. A slice position determination unit 125 determines each slice position and slice thickness for each of a plurality of volume data files. Determination of slice positions and slice thicknesses will be described in detail later.

A reproduction controller 118 controls readout of the data of a series of slice images from the volume data file storage unit 113 to cause the display unit 117 to display a series of slice images stored in the volume data file storage unit 113 as a moving image.

This reproduction display operation is associated with the periodic physiological motion of an subject. The periodic physiological motion is typically respiratory motion or pulsating motion. This embodiment can be applied to either of respiratory motion and pulsating motion. Assume that in the following description, the embodiment is applied to respiratory motion. The respiratory motion of the subject is measured by, for example, a respiration sensor 120. As is well known, respiratory operation is the expansion and contraction of the lung fields accompanying the reciprocal motion of the diaphragms. The abdominal region reciprocally moves back and forth accompanying the expansion and contraction of the lung fields. The respiration sensor 120 repeatedly measures the distance between a surface of the abdominal region of an subject and an external fixed point (a laser irradiation position) as a respiratory index by using, for example, a laser distance measuring technique. Temporal changes in distance reflect changes in respiratory state (respiratory phase) of the subject. A maximum value/minimum value specifying unit 123 specifies maximum and minimum values from temporal changes in respiratory index during an imaging period. For example, the time when, for example, the respiratory index indicates the minimum value represents an expiratory bottom time, whereas the respiratory index indicates the maximum value represents an inspiratory peak time. The interval between an expiratory bottom time and an inspiratory peak time represents a half period of a respiratory period.

Figure 4:
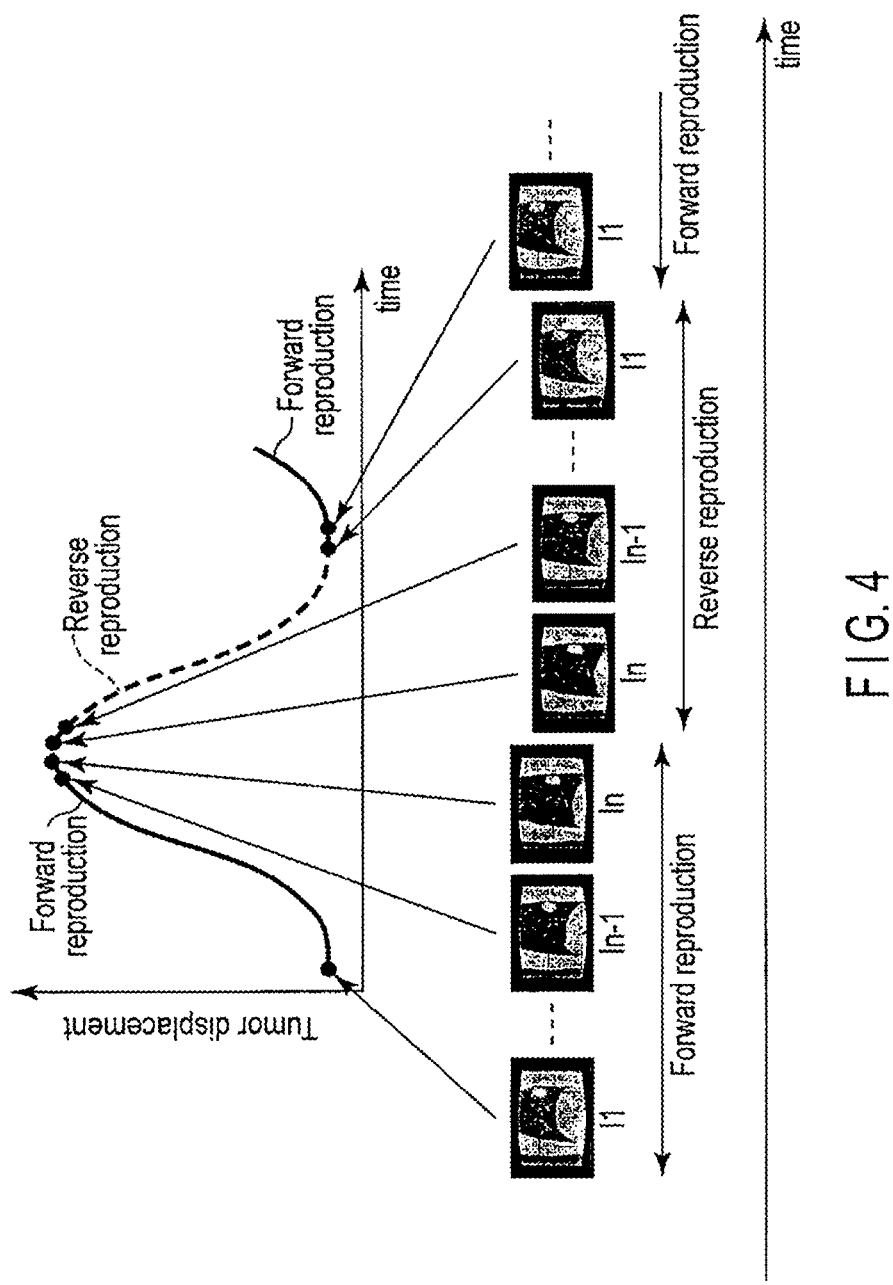
FIG. 4 is a view for explaining alternate reproduction by a reproduction controller in FIG. 1.

The reproduction controller 118 extracts, as images to be reproduced, a plurality of slice images, from a series of slice images stored in the volume data file storage unit 113, whose imaging times are included in the period from an expiratory bottom time to an inspiratory peak time. The reproduction controller 118 repeatedly reproduces a series of slice images specified as images to be reproduced. As shown in FIG. 4, the reproduction controller 118 reproduces a series of slice images in real time in the forward direction in the order of the imaging times respectively corresponding to the slice images (forward reproduction), and reproduces the slice images in real time in the reverse direction in the order of the imaging times respectively corresponding to the slice images (reverse reproduction), thus alternately and repeatedly performing forward reproduction and reverse reproduction. That is, reproduction directions are alternately changed. A moving image alternately reproduced within this almost half period of respiration is approximate to a moving image repeatedly reproduced in one respiratory period. In alternate reproduction limited to an almost half period, respiratory phases between boundary frames in alternate reproduction are almost identical. Obviously, therefore, a tissue distribution hardly displaces on the screen between boundary frames in alternate reproduction. This allows to visually recognize regional variation due to respiration with continuity. When observing a moving image with focus on, for example, a tumor, the observer need not greatly move his/her line of sight, resulting in convenience. In addition, even if an imaging period is set to a half respiratory period or a slightly longer period, it is possible to reproduce motion almost identical to that of a moving image obtained in one respiratory period or a longer period. A reduction in imaging period is most effective for reduction of radiation exposure.

The slice position determination unit 125 described above has a plurality of modes associated with slice determination. The slice position determination unit 125 can arbitrarily select one of the plurality of slice determination modes in accordance with the selection instruction input by the operator via an input device (not shown).

Figure 5:
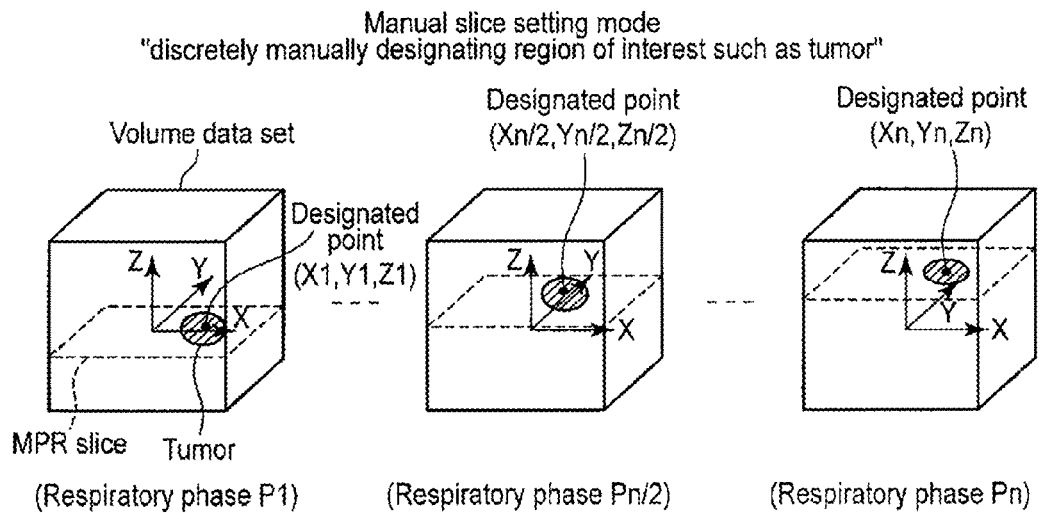
FIG. 5 is a view for explaining a manual slice setting mode by a slice position determination unit in FIG. 1.
Figure 6:
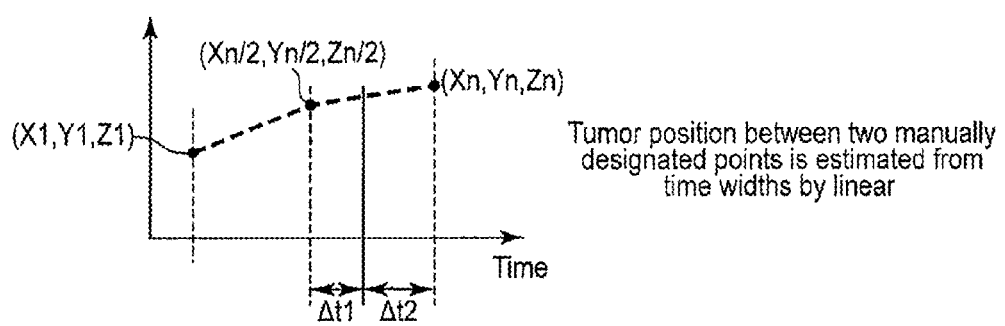
FIG. 6 is a graph for explaining slice position interpolation processing by the slice position determination unit in FIG. 1.

FIG. 5 is a view for explaining a manual slice determination mode. In the manual slice determination mode, an X-Y plane perpendicular to the Z-axis as a reference axis is set as a slice. While the manual slice determination mode is activated, the slice image generation unit 115 sets a common slice candidate parallel to the X-Y plane for several discrete volume data files of a series of volume data files. An initial slice candidate is set to, for example, an X-Y plane passing through the origin of an XYZ coordinate system. As target volume data files, for example, three volume data files at the two ends and middle of a series of volume data files are initially selected. The slice image generation unit 115 generates slice images associated with the initial slice using these three volume data files. The display unit 117 simultaneously or selectively displays the three slice images associated with the initial slice. The operator searches for a slice position at which an image of the region of interest (ROI) is displayed with the highest quality while moving the slice along the Z-axis via an input device (not shown), and designates, for example, a central point (to be referred to as a point of interest or designated point) of the region of interest on the slice image. The operator searches each of all the three volume data files for a slice, and designates a point of interest. The slice position determination unit 125 estimates a point of interest in each of the remaining volume data files between the three volume data files as manual designation targets by linear interpolation using two points designated on two volume data files on the two sides of the volume data file as the interpolation target on the time axis, as shown in FIG. 6. As a point of interest estimated, a point is determined which is located on a straight line connecting two designated points of interest on the two sides in a three-dimensional coordinate system, and is calculated by linear interpolation using time widths $\Delta t1$ and $\Delta t2$ between the time of the volume data file as the interpolation target and the times of the manually designated volume data files.

The slice image generation unit 115 determines slices respectively including the points of interest designated or interpolated in a plurality of volume data files and parallel to the X-Y plane with respect to the respective volume data files. It is also possible to manually designate a point of interest in each of all the volume data files.

The slice image generation unit 115 generates a plurality of slice images respectively corresponding to a plurality of volume data files in accordance with the set slices. The plurality of slice images are stored in the volume data file storage unit 113. The reproduction controller 118 controls readout from the volume data file storage unit 113 to the display unit 117 to alternately repeat forward reproduction and reverse reproduction of images as a moving image, as described above. The reproduction controller 118 performs read control and write control for the frame memory in the display unit 117 to independently shift the display position of each slice image so as to set the point of interest on each slice image to a specific position, typically the central position, on the display of the display unit 117.

Figure 14:
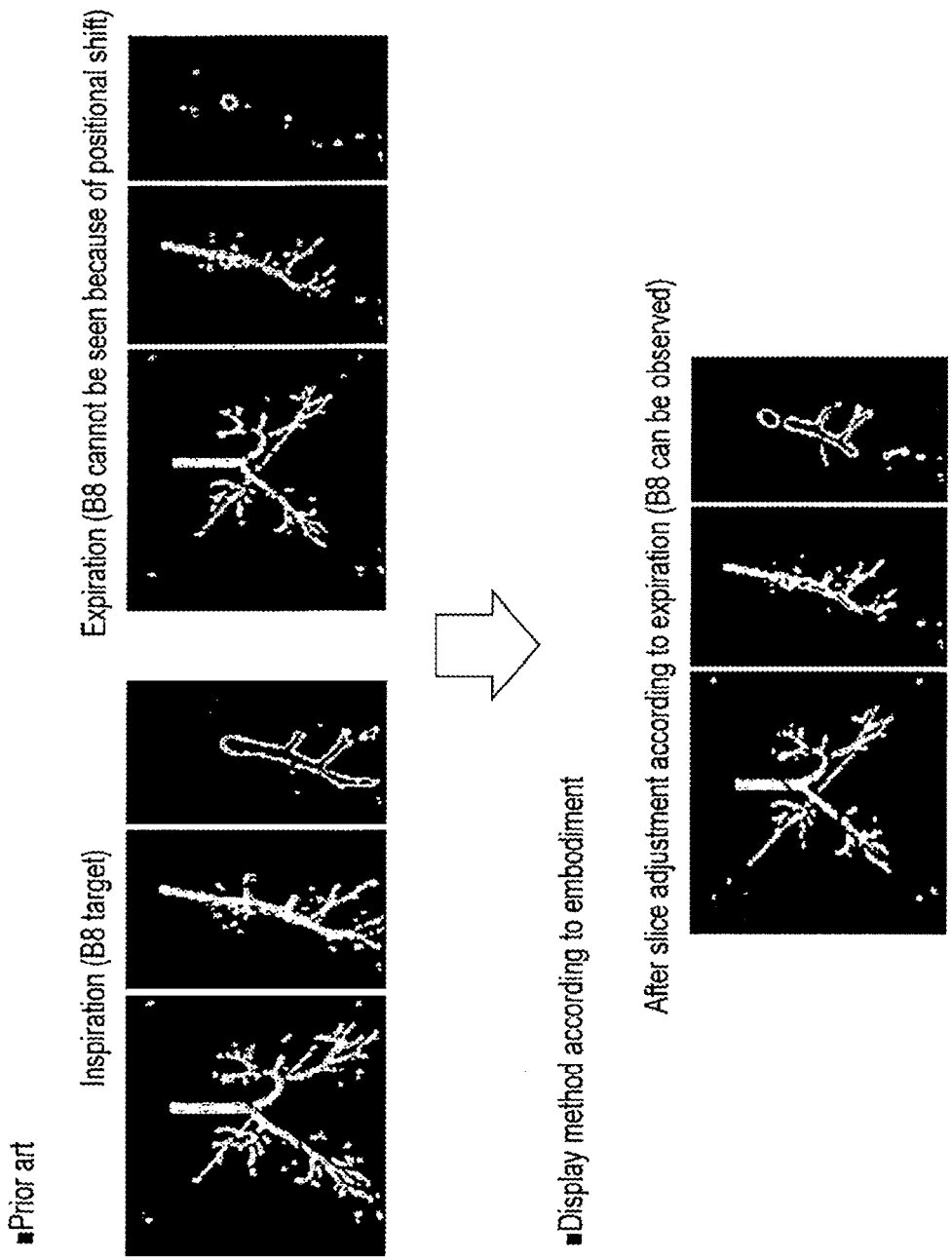
FIG. 14 is a view showing the effects obtained by this embodiment.

As exemplified by FIGS. 14 and 15, a slice image including a region of interest is always displayed in moving image reproduction, and an image of the region of interest is fixed to a specific position on a frame. This allows to suitable visual recognition of the region of interest on all the slice images, and also reduces the movement of line of sight, thus making it possible to effectively perform diagnosis on the adhesion of a tumor or the like.

Figure 7:
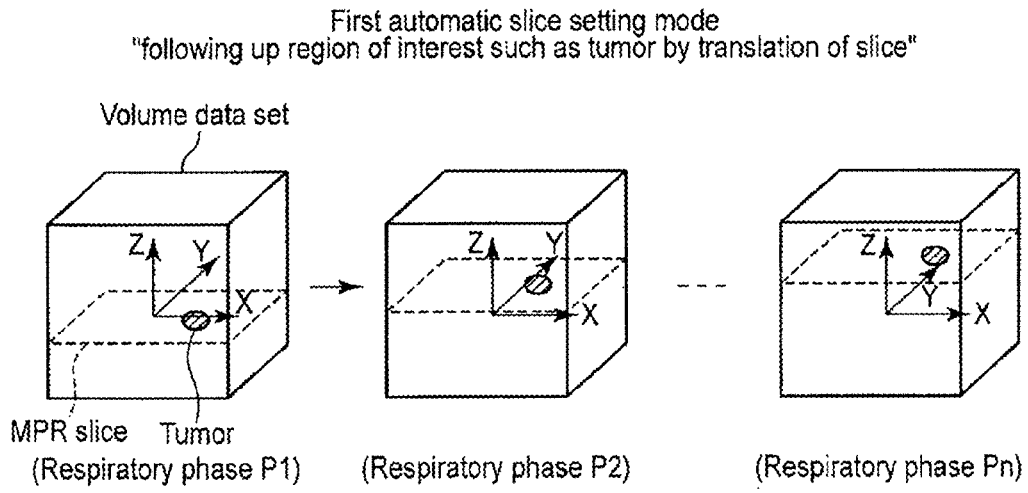
FIG. 7 is a view for explaining the first automatic slice setting mode by the slice position determination unit in FIG. 1.

FIG. 7 is a view for explaining the first automatic slice setting mode. In the first automatic slice setting mode, an X-Y plane perpendicular to the Z-axis as a reference axis is set as a slice. While the first automatic slice setting mode is activated, the slice image generation unit 115 generates a slice image associated with an initial candidate passing through an origin parallel to, for example, an X-Y plane with respect to a specific single volume data file as a target from a series of volume data files. A specific single volume data file is typically a volume data file nearest to the middle time among a series of volume data files. The operator searches for a slice on which an image of the region of interest is displayed with the highest quality while moving the candidate slice along the Z-axis via an input device (not shown), and designates a point in the region of interest on the slice image.

Figure 18:
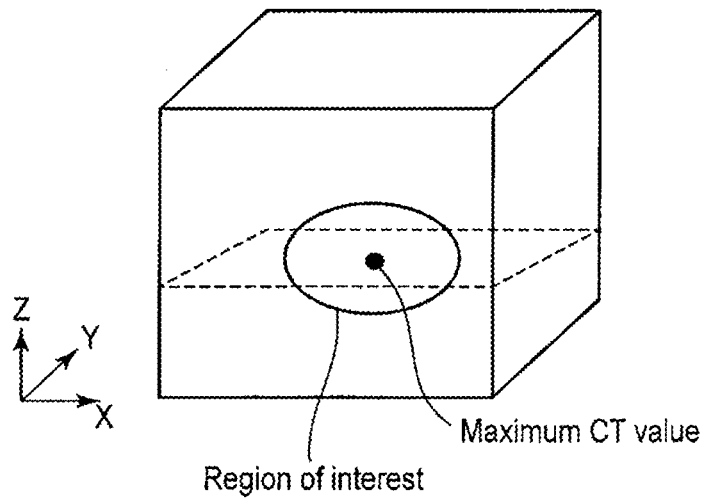
FIG. 18 is a view showing a slice example set by the first automatic slice setting mode in FIG. 7.

The slice position determination unit 125 extracts a three-dimensional region of interest from each of the remaining volume data files by threshold processing using the pixel value of a designated point or the average or median associated with a plurality of pixels within a local range centered on the designated point. The slice position determination unit 125 sets a point of interest inside each extracted region of interest. There are various variations of points of interest. As shown in FIG. 16, an example of a point of interest is a barycentric point or a point spaced apart from the barycentric point by a predetermined distance $\Delta d$ in the Z-axis direction. As shown in FIG. 17, another example of a point of interest is a point which passes through the barycenter, is parallel to the Z-axis, and divides a line segment having two ends at the edge of a region of interest at a predetermined distance ratio. As shown in FIG. 18, still another example of a point of interest is the central point of a pixel having the maximum CT value or minimum CT value in a region of interest. Although a barycenter is set initially, the operator can select arbitrary one of these points of interest. Note that the methods of setting points of interest described with reference to FIGS. 16, 17, and 18 can also be applied to the methods of designating designated points with respect to blood vessels and bronchi shown in FIGS. 9, 10, and 11.

Slice determination and moving image reproduction processing after a point of interest is set are the same as those described in association with the manual setting mode. A slice is determined, which includes a point of interest set for each volume data file and is perpendicular to an X-Y plane (a slice perpendicular to the Z-axis (reference axis)). The apparatus generates a slice image from a volume data file by MPR processing in accordance with the determined slice. Likewise, the apparatus generates slice images based on all the volume data files. The apparatus alternately repeats forward reproduction and reverse reproduction under the read control of the reproduction controller 118.

Figure 19:
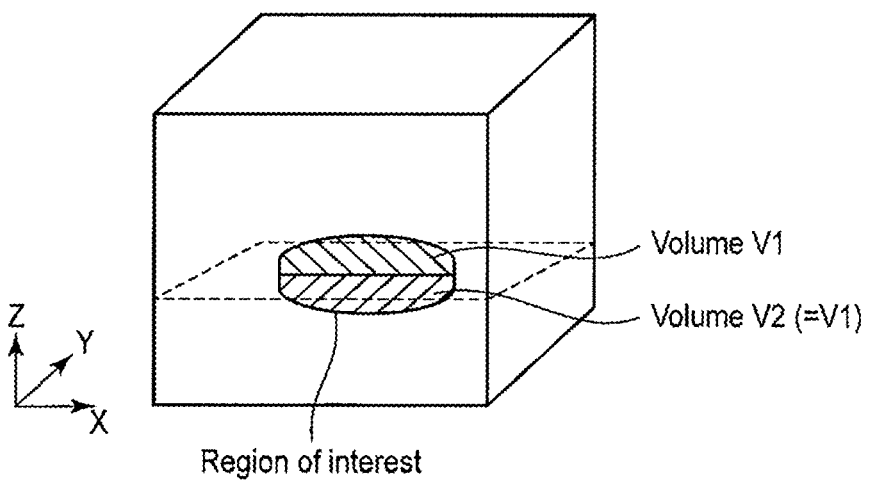
FIG. 19 is a view showing a slice example set by the first automatic slice setting mode in FIG. 7.

As shown in FIG. 19, it is possible to search for an X-Y plane which divides the volume of an extracted region of interest into two equal volumes and generate a slice image from a volume data file in accordance with the X-Y plane (slice).

Like the manual setting mode, the first automatic slice setting mode is suitable when a region of interest is in a massive form like a tumor.

Figure 8:
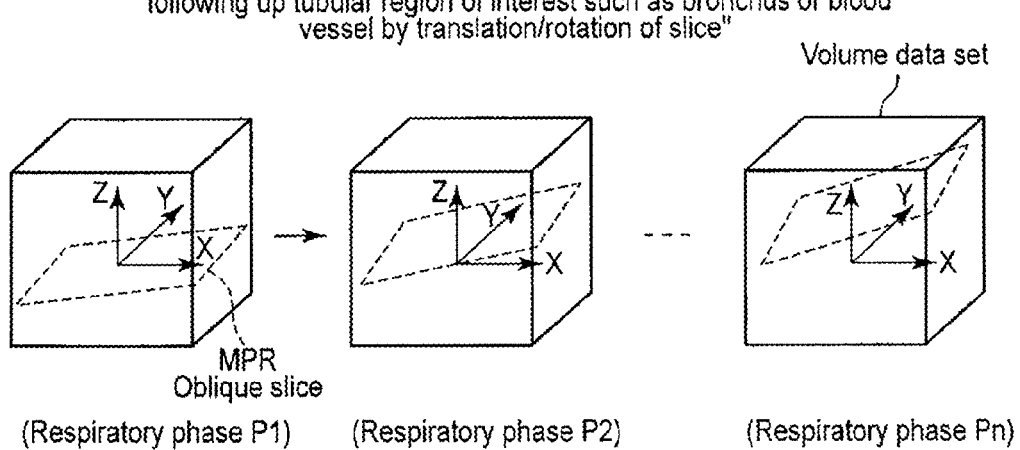
FIG. 8 is a view for explaining the second automatic slice setting mode by the slice position determination unit in FIG. 1.
Figure 9:
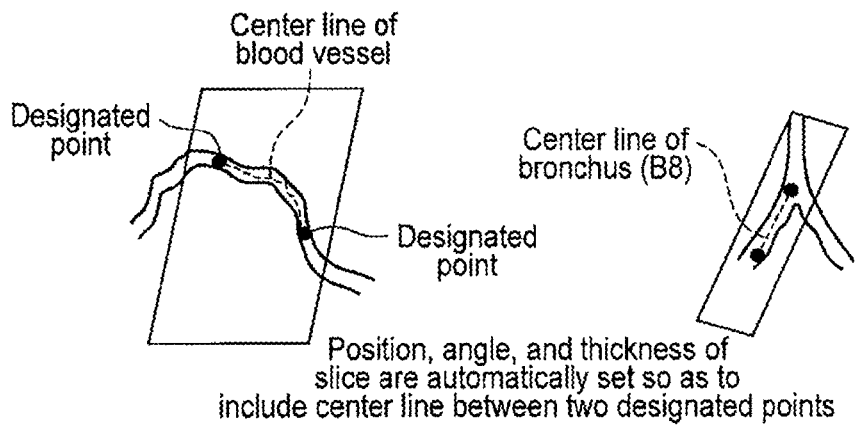
FIG. 9 is a view for additionally explaining the second automatic slice setting mode in FIG. 8.

FIG. 8 is a view for explaining the second automatic slice setting mode. The second automatic slice setting mode allows to set, as a slice, an oblique plane obliquely intersecting the Z-axis as a reference axis. The second automatic slice setting mode is suitable when targets are tubular regions such as bronchi and blood vessels. The slice position determination unit 125 extracts, for example, a blood vessel region from each of a series of volume data files by threshold processing. The operator sets a slice of interest including a stricture or the like in the extracted region of interest by designating two points on the two ends of the slice, as shown in FIG. 9. The slice position determination unit 125 specifies the center line of a blood vessel in the extracted blood vessel region which passes through the two designated points. The slice position determination unit 125 determines, for each of a plurality of volume data files, a slice position, oblique angles with respect to the X-, Y-, and Z-axes, and a slice thickness so as to include the center line of the blood vessel between the two designated points.

Slice image generation processing and moving image reproduction processing after slice determination are almost the same as those described in association with the manual setting mode described above. In this mode, the apparatus generates a slice image by, for example, integrating a plurality of voxel values along a direction (ray) perpendicular to the slice or extracting the maximum value from the plurality of voxel values. The apparatus generates a plurality of slice images according to the slices determined for the respective volume data files. The apparatus alternately repeats forward reproduction and reverse reproduction of a plurality of slice images under the read control of the reproduction controller 118.

In the second automatic slice setting mode, it is possible to always visually recognize, on the screen, an overall slice of interest such as a blood vessel bent in a complicated form such as a coronary artery of the heart.

The second automatic slice setting mode which defines an oblique slice can be applied to a tumor or the like which has a massive form. In this case, as shown in FIG. 20, an oblique slice is set on a plane which passes through the barycenter of an extracted region of interest and is defined by, for example, two line segments indicating the maximum and minimum diameters or the maximum diameter and the second longest diameter of the distances (diameters) of line segments each having two ends on the edge of the region of interest. Another example is to set an oblique slice on a plane on which an extracted region of interest exhibits the largest slice area, as shown in FIG. 21.

Figure 10:
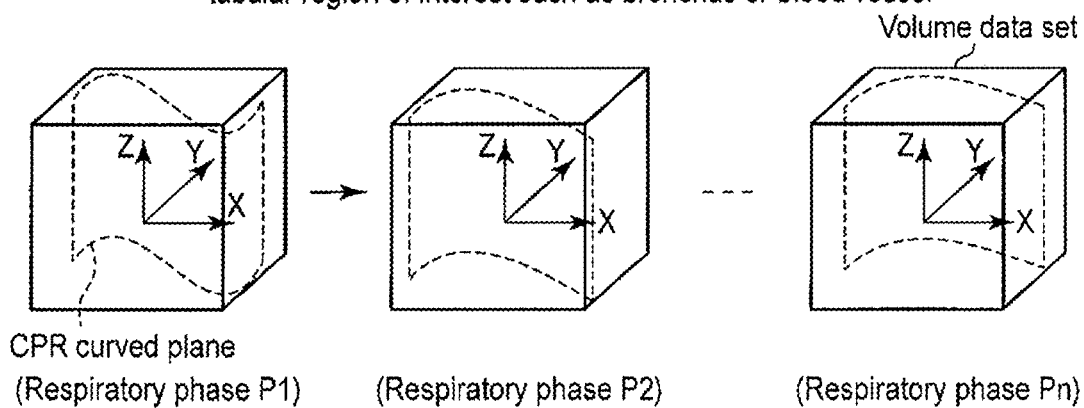
FIG. 10 is a view for explaining the third automatic slice setting mode by the slice position determination unit in FIG. 1.
Figure 11:
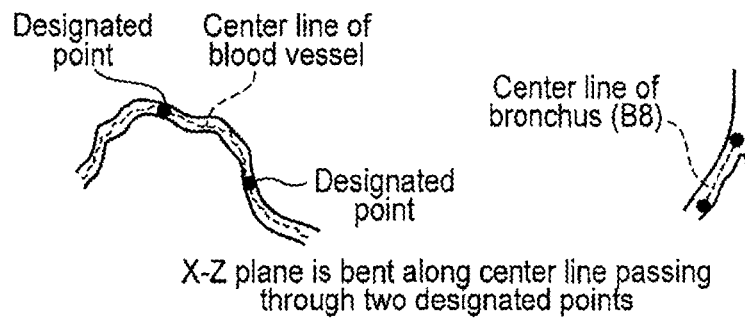
FIG. 11 is a view for additionally explaining the third automatic slice setting mode in FIG. 10.

FIG. 10 is a view for explaining the third automatic slice setting mode. The third automatic slice setting mode is also suitable when targets are tubular regions such as bronchi and blood vessels. The slice position determination unit 125 extracts, for example, a blood vessel region from each of a series of volume data files by threshold processing. The operator sets a slice of interest including a stricture or the like in the extracted region of interest by designating two points on the two ends of the slice, as shown in FIG. 11. Note that the operator may designate one point on the peripheral side of a blood vessel, and the apparatus automatically traces up to an upper portion of the blood vessel, thereby setting a slice of interest between the periphery of the blood vessel and the upper portion of the blood vessel.

The slice position determination unit 125 specifies the center line of a blood vessel in the extracted blood vessel region, which passes through the two designated points. A slice perpendicular to an X-Y plane is bent along a projection image of the center line of the blood vessel between the two designated points on the X-Y plane while being kept perpendicular to the X-Y plane. This will determine a slice (curved slice) with respect to each of a plurality of volume data files.

Slice image generation processing and moving image reproduction processing after slice determination are almost the same as those described in association with the manual setting mode described above. The apparatus generates a plurality of slice images respectively corresponding to a plurality of volume data files in accordance with curved slices determined for the respective volume data files. The apparatus then repeats forward reproduction and reverse production under the read control of the reproduction controller 118.

The third automatic slice setting mode allows to always visually recognize, on the screen, an overall slice of interest such as a blood vessel bent in a complicated form more precisely than in the second automatic slice setting mode.

Figure 12:
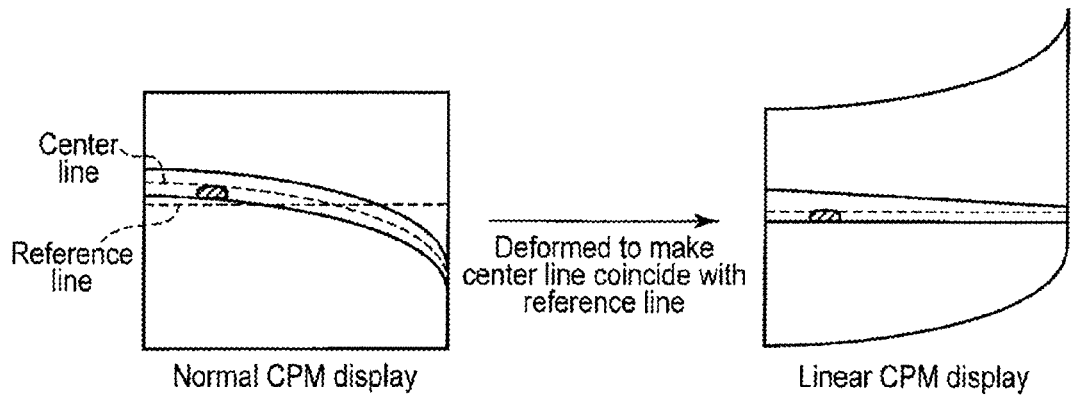
FIG. 12 is a view showing the first image processing for the slice image generated in the third automatic slice setting mode in FIG. 3.
Figure 13:
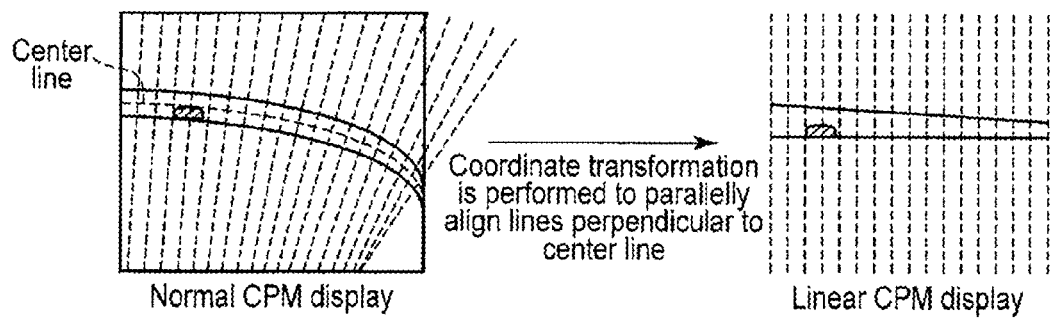
FIG. 13 is a view showing the second image processing for the slice image generated in the third automatic slice setting mode in FIG. 3.

Note that the slice image generation unit 115 may deform an image of a blood vessel running in a complicated manner on a slice image generated in the second or third automatic slice setting mode into a linear image by coordinate transformation, as shown in FIG. 12. As an example of coordinate transformation, as shown in FIG. 13, a plurality of line segments perpendicular to the center line of a blood vessel at the center are arranged, and a plurality of pixel arrays on the plurality of line segments are rearranged into an orthogonal coordinate system.

Some embodiments of the present invention have been described above. However, these embodiments are presented merely as examples and are not intended to restrict the scope of the invention. These embodiments can be carried out in various other forms, and various omissions, replacements, and alterations can be made without departing from the gist of the invention. The embodiments and their modifications are also incorporated in the scope and the gist of the invention as well as in the invention described in the claims and their equivalents.

REFERENCE SIGNS LIST

100 . . . gantry unit
101 . . . X-ray tube

102 . . . rotating frame
103 . . . two-dimensional detector
104 . . . data acquisition device
106 . . . preprocessing unit
107 . . . gantry driving unit
109 . . . high voltage generator
110 . . . host controller
112 . . . projection data storage unit
113 . . . volume data file storage unit
115 . . . slice image generation unit
116 . . . cone beam reconstruction processing unit
117 . . . display unit (display)
118 . . . reproduction controller
120 . . . respiration sensor
121 . . . respiratory waveform storage unit
123 . . . maximum value/minimum value specifying unit
125 . . . slice position determination unit While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus, comprising:
   a storage unit configured to store a plurality of volume data files associated with a three-dimensional region of an subject;
   an image generation unit configured to generate, based on designation of a first slice, a first slice image from a first volume data file of the plurality of volume data files; and
   a slice determination unit configured to automatically determine, based on designation of a first point on the region in the first slice image, corresponding slices in each volume data corresponding to the plurality of volume data files other than the first volume data file,
   wherein the slice determination unit is configured to determine, as each slice, a plane including a barycenter of a region of interest extracted from the corresponding volume data file.

2. The medical image processing apparatus of claim 1, wherein the slice determination unit is configured to determine the slices based on corresponding regions of interest extracted from the plurality of volume data files other than the first volume data file.

3. The medical image processing apparatus of claim 1, wherein the determined slices are perpendicular to a reference axis.

4. The medical image processing apparatus of claim 1, wherein the slices are set obliquely with respect to a reference axis.

5. The medical image processing apparatus of claim 1, wherein the first slice is manually set for the first volume data file.

6. The medical image processing apparatus of claim 1, further comprising:
   a data storage unit configured to store data repeatedly acquired in a first period with respect to a three-dimensional region of the subject as a target; and
   a volume data generation unit configured to generate the plurality of volume data files in a second period shorter than the first period based on the acquired data.

7. The medical image processing apparatus of claim 1, further comprising a display configured to alternately reproduce and display a plurality of slice images as a moving image in a forward direction and a reverse direction.

8. The medical image processing apparatus of claim 7, wherein a display position of each slice image of the plurality of slice images is controlled to fix a position of a region of interest designed by an operator in each of the plurality of displayed slice images to a same position on a display screen.

9. The medical image processing apparatus of claim 1, wherein the image generation unit is further configured to generate slice images corresponding to the determined slices, based on the plurality of volume data files other than the first volume data file.

10. An X-ray computed tomography apparatus, comprising:
    an acquisition unit configured to repeatedly acquire projection data associated with a three-dimensional region of an subject;
    a reconstruction unit configured to reconstruct a plurality of volume data files from the projection data;
    an image generation unit configured to generate, based on designation of a first slice, a first slice image from a first volume data file of the plurality of reconstructed volume data files; and
    a slice determination unit configured to automatically determine, based on designation of a first point on the region in the first slice image, corresponding slices in each volume data corresponding to the plurality of volume data files other than the first volume data file,
    wherein the slice determination unit is configured to determine, as each slice, a plane including a barycenter of a region of interest extracted from the corresponding volume data file.

* * * * *